United States Patent
Sasaki et al.

[11] Patent Number: 5,990,353
[45] Date of Patent: Nov. 23, 1999

[54] PROCESS FOR PRODUCING ARYLSULFONYLUREIDE COMPOUNDS

[75] Inventors: Nobuaki Sasaki, Kyoto; Bunji Sawano, Osaka; Mansuke Matsumoto, Hyogo; Toshihiko Kawabata, Osaka, all of Japan

[73] Assignee: Yamamoto Chemicals, Inc., Osaka, Japan

[21] Appl. No.: 09/081,203

[22] Filed: May 19, 1998

[30] Foreign Application Priority Data

May 20, 1997 [JP] Japan .................................. 9-147164

[51] Int. Cl.$^6$ .................................................. C07C 311/52
[52] U.S. Cl. ................................................. 564/42; 564/39
[58] Field of Search ......................................... 564/42, 39

[56] References Cited

U.S. PATENT DOCUMENTS

| | | | |
|---|---|---|---|
| 3,150,180 | 9/1964 | Hayman et al. | 564/42 |
| 3,384,757 | 5/1968 | Ruschig et al. | 564/42 |

FOREIGN PATENT DOCUMENTS

| | | | |
|---|---|---|---|
| 51-48220A | 6/1993 | Japan | . |
| 53-01455A | 11/1993 | Japan | . |
| 62-39030A | 8/1994 | Japan | . |

*Primary Examiner*—Shailendra Kumar
*Attorney, Agent, or Firm*—Birch, Stewart, Kolasch & Birch, LLP

[57] ABSTRACT

The arylsulfonylureide compound which is of value as a color developer is provided in high yield and high purity by a simple procedure. The technology of the invention for producing an arylsulfonylureide compound of general formula (1)

$$(Ar^1\text{—}SO_2NHCONH)_n\text{—}Ar^2 \qquad (1)$$

wherein $Ar^1$ represents an aromatic residue; $Ar^2$ represents a bivalent or trivalent aromatic residue; n represents an integer of 2 or 3 comprises reacting an arylsulfonamide alkali metal salt of general formula (2)

$$Ar^1\text{—}SO_2NH\cdot B \qquad (2)$$

wherein B represents an alkali metal with an aromatic isocyanate compound of general formula (3)

$$Ar^2\text{—}(NCO)_n \qquad (3)$$

in at least one solvent selected from the class consisting of acetonitrile, acetone, methyl ethyl ketone, diethyl ketone, methyl isobutyl ketone, tetrahydrofuran, ethyl acetate, and butyl acetate and containing 1 to 10 weight % of water in a state of suspension being maintained throughout the reaction and eliminating the alkali metal from the resulting arylsulfonylureide compound alkali metal salt in the same solvent.

4 Claims, No Drawings

PROCESS FOR PRODUCING ARYLSULFONYLUREIDE COMPOUNDS

TECHNICAL FIELD

The present invention relates to a process for producing an organic compound containing two or three defined arylsulfonylureide groups. More particularly, the invention relates to a process for producing an arylsulfonylureide compound which finds application as a color developer for a thermal recording material with improved oil resistance and plasticizer resistance of developed color images.

PRIOR ART

The thermal recording material has the advantage of low cost and ease of maintenance of the necessary hardware but has the disadvantage that because the color reaction involved is reversible, the developed color image tends to fade with time. This fading is accelerated by exposure to light or contact with a plasticizer or oil, so that the developed color image may fade out completely under the most unfavorable conditions.

Processes for production of arylsulfonylureide compounds, which are color developers useful for overcoming this drawback of fading, particularly lack of resistance to oil and plasticizers, are disclosed in Japanese Kokai Tokkyo Koho H5-148220, Kokai Tokkyo Koho H5-301455, and Kokai Tokkyo Koho H6-239030.

In the gazette of Kokai Tokkyo Koho H5-148220, the following alternative routes (1) and (2) to 4,4'-bis(p-toluenesulfonylaminocarbonylamino)diphenylmethane are described in the right top to the left bottom columns of page 3.

(1) Synthesis starting with 2 moles of p-toluenesulfonyl isocyanate and 1 mole of 4,4'-diaminodiphenylmethane (2) Synthesis starting with 2 moles of p-toluenesulfonamide and 1 mole of 4,4'-diphenylmethane diisocyanate Referring to the reaction solvent for use in said processes (1) and (2), the above gazette mentions that non-aromatic solvents, particularly halogenated aliphatic compounds, aliphatic nitriles, aliphatic esters, aliphatic ethers, and aliphatic ketones, are preferred.

However, the starting p-toluenesulfonyl isocyanate for process (1) above is not readily available in practically useful quantities and, moreover, is expensive, thus being unsuited as a raw material for commercial-scale production.

On the other hand, the starting compounds for the above process 2 are readily available but the progress of the reaction is very slow.

The gazette of Kokai Tokkyo Koho H5-301455 discloses a process for producing an arylsulfonylaminocarbonylamino-containing compound which comprises reacting an arylsulfonylcarbamic acid ester with a polyamino compound and, immediately before completion of the reaction, adding an arylsulfonyl isocyanate so as to cause it to react with the unreacted amino compound. This process is disadvantageous in that the arylsulfonylcarbamic acid ester is not so readily available and in that the amount of the arylsulfonyl isocyanate to be added just before completion of the reaction cannot be easily programmed. For if the amount of the arylsulfonyl isocyanate added is too small, the product yield will not be satisfactory. On the other hand, if the amount is too large, insoluble matter will form to detract from the efficiency of purification. Moreover, the arylsulfonyl isocyanate is expensive, so that the process is not satisfactory in terms of production cost.

The gazette of Kokai Tokkyo Koho H6-239030 discloses a process for producing an organic compound containing two or more arylsulfonyl(thio)ureide groups which comprises dissolving an arylsulfonamide in an aqueous solution of an alkali metal salt to prepare an aqueous solution of the arylsulfonamide alkali metal salt on the one hand, dissolving an aromatic polyiso(thio)cyanate in an organic solvent with a water solubility of not less than 50 weight % at the reaction temperature on the other hand, and allowing them to react in a homogeneous mixture of said organic solvent and water.

However, this process is hardly capable of providing an arylsulfonyl(thio)ureide compound of high purity in acceptable yield. The reason appears to be that since an aqueous solution of the arylsulfonamide alkali metal salt is used as a reactant and the reaction medium therefore contains a comparatively large proportion of water, the decomposition of the aromatic polyiso(thio)cyanate by water gives rise to a large amount of byproducts.

OBJECT AND SUMMARY OF THE INVENTION

The object of the present invention is to provide a process by which an arylsulfonylureide compound can be produced in high yield and high purity by an expedient procedure.

The inventors of the present invention did much research and have perfected the invention herein disclosed.

The present invention, therefore, is directed to a process for producing an arylsulfonylureide compound of general formula (1)

$$(Ar^1-SO_2NHCONH)_n-Ar^2 \quad (1)$$

wherein $Ar^1$ represents an aromatic residue; $Ar^2$ represents a bivalent or trivalent aromatic residue; n represents an integer of 2 or 3; provided that when $Ar^2$ represents a bivalent residue, n is equal to 2 and that when $Ar^2$ is a trivalent residue, n is equal to 3 which comprises reacting an arylsulfonamide alkali metal salt of general formula (2)

$$Ar^1-SO_2NH.B \quad (2)$$

wherein $Ar^1$ has the same meaning as $Ar^1$ in general formula (1); B represents an alkali metal with an aromatic isocyanate compound of general formula (3)

$$Ar^2-(NCO)_n \quad (3)$$

wherein $Ar^2$ and n have the same meanings as $Ar^2$ and n, respectively, in general formula (1) in at least one solvent selected from the class consisting of acetonitrile, acetone, methyl ethyl ketone, diethyl ketone, methyl isobutyl ketone, tetrahydrofuran, ethyl acetate, and butyl acetate and containing 1 to 10 weight % of water in a state of suspension being maintained throughout the reaction and eliminating the alkali metal from the resulting arylsulfonylureide compound alkali metal salt in said solvent.

DETAILED DESCRIPTION OF THE INVENTION

The production process of the invention is now described in detail.

Referring to general formulas (1) and (2), the aromatic residue represented by $Ar^1$ is preferably a benzene series aromatic residue which may be substituted. The particularly preferred residue is phenyl or naphthyl. The substituent group which is preferred includes alkyl groups of 1–6 carbon atoms, alkoxy groups of 1–6 carbon atoms, and halogen. Particularly preferred examples of $Ar^1$ are phenyl, tolyl, chlorophenyl, and 2,4-xylyl, among others.

The arylsulfonamide as a starting compound for said arylsulfonamide alkali metal salt represented by general formula (2) includes but is not limited to benzenesulfonamide, toluenesulfonamide, chlorobenzenesulfonamide, bromobenzenesulfonamide, methoxybenzenesulfonamide, ethoxybenzenesulfonamide, ethylbenzenesulfonamide, xylenesulfonamide, diethylbenzenesulfonamide, trimethylbenzenesulfonamide, ethoxytoluenesulfonamide, methoxytoluenesulfonamide, chlorotoluenesulfonamide, chloromethoxybenzenesulfonamide, chloroethoxybenzenesulfonamide, naphthalenesulfonamide, methylnaphthalenesulfonamide, dimethylnaphthalenesulfonamide, methoxynaphthalenesulfonamide, and chloronaphthalenesulfonamide.

The alkali metal represented by B in general formula (2) includes lithium, sodium, potassium, etc., although sodium or potassium is preferred.

Referring to general formulas (1) and (3), the bivalent or trivalent aromatic residue represented by $Ar^2$ includes (A) groups having a benzene or naphthalene nucleus, (B) groups having a biphenyl nucleus, (C) groups having a diphenylmethane or diphenylethane nucleus, (D) groups having a phenylenedibenzyl nucleus, (E) groups having a triphenylmethane nucleus, (F) groups having a triphenylamine nucleus, (G) groups having a diphenyl ketone nucleus, (H) groups having a diphenylsulfone nucleus, (I) groups having a diphenyl ether nucleus, (J) groups having diphenyl sulfide nucleus, and (K) groups having triphenyl phosphate nucleus, among others. Specifically, the following groups can be used.

(A)
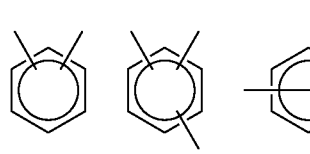

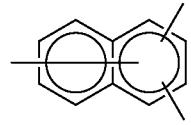

(B)
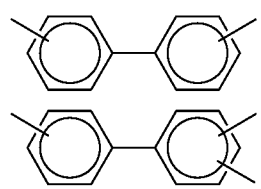

(C)
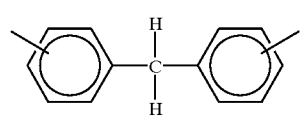

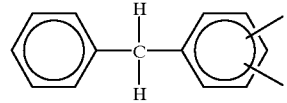

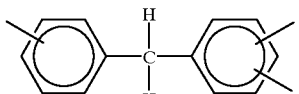

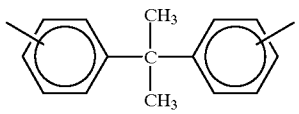

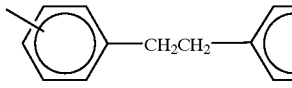

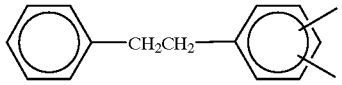

(D)
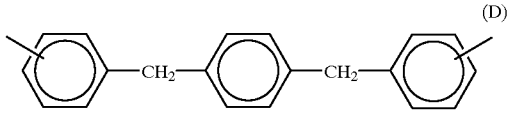

(E)
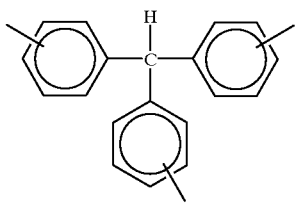

(F)
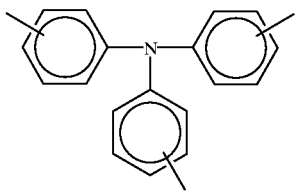

(G)
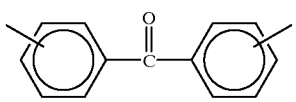

(H)
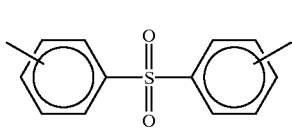

(I)
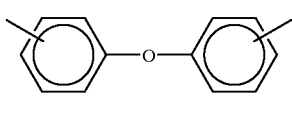

(J)
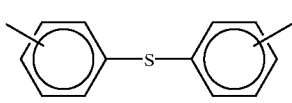

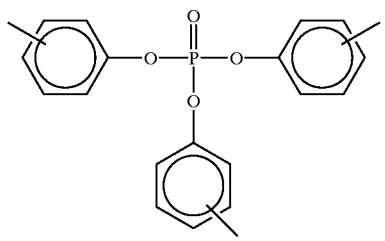
(K)

Among the above aromatic groups, (A) those having a benzene or naphthalene nucleus and (C) those having a diphenylmethane or diphenylethane nucleus are preferred.

The particularly preferred species of $Ar^2$ includes 1,2-phenylene, 1,4-phenylene, 2,4-tolylene, 2,6-tolylene, 1,4-naphthylene, 1,5-naphthylene, 1,8-naphthylene, 2,6-naphthylene, methylenebis(1,4-phenylene), and 2,2-propylenebis(1,4-phenylene).

The aromatic isocyanate compound of general formula (3) includes but is not limited to 1,3-phenylene-diisocyanate, 1,4-phenylene-diisocyanate, 2,4-tolylene-diisocyanate, 2,6-tolylene-diisocyanate, 2,5-tolylene-diisocyanate, 3,5-tolylene-diisocyanate, 1,3-dimethylbenzene-2,4-diisocyanate, 1,3-dimethylbenzene-4,6-diisocyanate, 1,4-dimethylbenzene-2,5-diisocyanate, ethylbenzene-2,4-diisocyanate, naphthalene-1,4-diisocyanate, naphthalene-1,5-diisocyanate, naphthalene-2,6-diisocyanate, naphthalene-2,7-diisocyanate, biphenyl-2,4'-diisocyanate, biphenyl-4,4'-diisocyanate, 3,3'-dimethylbiphenyl-4,4'-diisocyanate, 3,3'-dimethoxybiphenyl-4,4'-diisocyanate, 2-nitrobiphenyl-4,4'-diisocyanate, diphenylmethane-4,4'-diisocyanate, 2,2'-dimethyldiphenylmethane-4,4'-diisocyanate, diphenyldimethylmethane-4,4'-diisocyanate, 2,5,2',5'-tetramethyldiphenylmethane-4,4'-diisocyanate, 3,3'-dimethoxydiphenylmethane-4,4'-diisocyanate, 4,4'-dimethoxydiphenylmethane-3,3'-diisocyanate, 4,4'-diethoxydiphenylmethane-3,3'-diisocyanate, 2,2'-dimethyl-5,5'-dimethoxydiphenylmethane-4,4'-diisocyanate, 3,3'-dichlorodiphenylmethane-4,4'-diisocyanate, 1,2-diphenylethane-p,p'-diisocyanate, 1,2-diphenylethane-o,p-diisocyanate, benzophenone-3,3'-diisocyanate, α,β-diphenylethane-2,4-diisocyanate, toluene-2,4,6-triisocyanate, 1,3,5-trimethylbenzene-2,4,6-triisocyanate, naphthalene-1,3,7-triisocyanate, biphenyl-2,4,4'-triisocyanate, diphenylmethane-2,4,4'-triisocyanate, 3-methyldiphenylmethane-4,6,4'-triisocyanate, p-phenylenedibenzyl-4,4'-diisocyanate, triphenylmethane-4,4',4''-triisocyanate, triphenylamine-4,4',4''-triisocyanate, 3,6-dimethoxytriphenylamine-4,4',4''-triisocyanate, and tris-4,4',4''-isocyanatophenylphosphate.

The arylsulfonylureide compound of general formula (1) which can be produced in accordance with the present invention includes but is not limited to 1,3-bis[N'-(p-toluenesulfonyl)ureido]benzene, 1,4-bis[N'-(p-toluenesulfonyl)ureido]benzene, 2,4-bis[N'-(p-toluenesulfonyl)ureido]toluene, 2,6-bis[N'-(p-toluenesulfonyl)ureido]toluene, 2,4-bis[N'-(o-toluenesulfonyl)ureido]toluene, 2,4-bis[N'-(o-chlorobenzene)ureido]toluene, 2,4-bis[N'-(naphthalene-1-sulfonyl)ureido]toluene, 2,4-bis[N'-(benzenesulfonyl)ureido]toluene, 2,5-bis[N'-(p-toluenesulfonyl)ureido]toluene, 3,5-bis[N'-(p-toluenesulfonyl)ureido]toluene, 1,3-dimethyl-2,4-bis[N'-(p-toluenesulfonyl)ureido]benzene, 1,3-dimethyl-4,6-bis[N'-(o-toluenesulfonyl)ureido]benzene, 1,3-dimethyl-2,5-bis[N'-(p-toluenesulfonyl)ureido]benzene, 2,4-bis[N'-(p-toluenesulfonyl)ureido]ethylbenzene, 4,4'-bis[N'-(p-toluenesulfonyl)ureido]diphenylmethane, 4,4'-bis[N'-(o-toluenesulfonyl)ureido]diphenylmethane, 4,4'-bis[N'-(p-methoxybenzenesulfonyl)ureido]diphenylmethane, 4,4'-bis[N'-(p-chlorobenzenesulfonyl)ureido]diphenylmethane, 4,4'-bis[N'-(p-ethylbenzenesulfonyl)ureido]diphenylmethane, 4,4'-bis[N'-(p-benzenesulfonyl)ureido]diphenylmethane, 4,4'-bis[N'-(naphthalene-2-sulfonyl)ureido]diphenylmethane, 2,2'-dimethyl-4,4'-bis[N'-(p-toluenesulfonyl)ureido]diphenylmethane, 2,5,2',5'-tetramethyl-4,4'-bis[N'-(p-toluenesulfonyl)ureido]diphenylmethane, 3,3'-dimethoxy-4,4'-bis[N'-(p-toluenesulfonyl)ureido]diphenylmethane, 4,4'-dimethoxy-3,3'-bis[N'-(p-toluenesulfonyl)ureido]diphenylmethane, 2,2'-dimethyl-5,5'-dimethoxy-4,4'-bis[N'-(o-toluenesulfonyl)ureido]diphenylmethane, 4,4'-bis[N'-(2'',4''-dimethylbenzenesulfonyl)ureido]diphenylmethane, 4,4'-bis[N'-(2'',4'',6''-trimethylbenzenesulfonyl)ureido]diphenylmethane, 4,4'-bis[N'-(2''-ethoxy-4''-methylbenzenesulfonyl)ureido]diphenylmethane, 4,4'-bis[N'-(2''-methoxy-4''-methylbenzenesulfonyl)ureido]diphenylmethane, 4,4'-bis[N'-(2''-chloro-4''-methylbenzenesulfonyl)ureido]diphenylmethane, 4,4'-bis[N'-(2''-chloro-4''-methoxybenzenesulfonyl)ureido]diphenylmethane, 4,4'-bis[N'-(2''-chloro-4''-ethoxybenzenesulfonyl)ureido]diphenylmethane, 4,4'-bis[N'-(naphthalene-2''-sulfonyl)ureido]diphenylmethane, 4,4''-bis[N'-(naphthalene-1''-sulfonyl)ureido]diphenylmethane, 4,4'-bis[N'-(4''-methylnaphthalene-2''-sulfonyl)ureido]diphenylmethane, 4,4'-bis[N'-(4''-methoxynaphthalene-2''-sulfonyl)ureido]diphenylmethane, 2,4-bis[N'-(p-toluenesulfonyl)ureido]-α,β-diphenylethane, 3,3'-bis[N'-(p-toluenesulfonyl)ureido]benzophenone, 2,2'-bis[4',4''-{N'-(p-toluenesulfonyl)ureido}phenyl]propane, 2,2'-bis{3,3'-dichloro-4',4''-[N'-(p-toluenesulfonyl)ureido]phenyl}propane, 1,4-bis[N'-(p-toluenesulfonyl)ureido]naphthalene, 1,5-bis[N'-(o-toluenesulfonyl)ureido]naphthalene, 2,6-bis[N'-(o-toluenesulfonyl)ureido]naphthalene, 2,7-bis[N'-(o-methoxytoluenesulfonyl)ureido]naphthalene, 2,4'-bis[N'-(o-toluenesulfonyl)ureido]diphenyl, 4,4'-bis[N'-(o-bromobenzenesulfonyl)ureido]diphenyl, 3,3'-dimethyl-4,4'-bis[N'-(p-toluenesulfonyl)ureido]diphenyl, 3,3'-dimethoxy-4,4'-bis[N'-(p-toluenesulfonyl)ureido]diphenyl, 2,4,6-tris[N'-(p-toluenesulfonyl)ureido]toluene, 2,4,6-tris[N'-(o-toluenesulfonyl)ureido]benzene, 1,3,7-tris[N'-(benzenesulfonyl)ureido]naphthalene, 2,4,4'-tris[N'-(p-toluenesulfonyl)ureido]diphenylmethane, 4,4',4''-tris[N'-(p-toluenesulfonyl)ureido]triphenylmethane, 4,4',4''-tris[N'-(p-toluenesulfonyl)ureido]triphenylamine, 3,6-dimethoxy-4,4',4''-tris[N'-(p-toluenesulfonyl)ureido]triphenylamine, and 4,4',4''-tris[N'-(p-toluenesulfonyl)ureido]triphosphate.

In the production process according to the invention, the arylsulfonamide alkali metal salt of general formula (2), not in the form of an aqueous solution, is reacted with the aromatic isocyanate compound of general formula (3) in at least one solvent selected from the class consisting of acetonitrile, acetone, methyl ethyl ketone, diethyl ketone, methyl isobutyl ketone, tetrahydrofuran, ethyl acetate, and butyl acetate and containing 1–10 weight % of water (hereinafter referred to as the water-containing solvent) with a state of suspension being maintained throughout the reaction to produce an arylsulfonylureide alkali metal salt of the following formula (1').

$$(Ar^1\text{—}SO_2NHCON)_n\text{—}Ar^2.B_n \tag{1'}$$

wherein $Ar^1$, $Ar^2$, and n are as defined in general formula (1).

Using a mineral acid, the alkali metal is removed, in the form of an inorganic salt, from the above arylsulfonylureide compound to thereby provide the objective arylsulfonylureide compound of high purity in good yield.

The molar ratio of the arylsulfonamide alkali metal salt of general formula (2) to the aromatic isocyanate compound of general formula (3) wherein n=2 in general formula (3) is preferably (2):(3)=1.8:1–2.4:1 and more preferably (2):(3)= 2:1–2.2:1. When n=3 in general formula (3), the molar ratio is preferably (2):(3)=2.7:1–3.6:1 and more preferably (2): (3)=3:1–3.3:1.

The proportion of the water-containing solvent is 1–20 parts by weight and preferably 3–10 parts by weight based on the weight of the arylsulfonamide alkali metal salt of general formula (2). When the proportion of said solvent is less than 1 part by weight, the reaction system can hardly be stirred efficiently. Conversely if the proportion is greater than 20 parts by weight, the state of suspension may not be sustained but a solution will be formed in certain cases.

In practicing the process of the invention, the preferred procedure comprises adding the aromatic isocyanate compound (3) to a suspension of the arylsulfonamide alkali metal salt (2) in the water-containing solvent, for the formation of byproducts will then be suppressed.

Because, in the process of the invention, a specified organic solvent, e.g. acetonitrile, with a limited water content, i.e. 1–10 weight % $H_2O$, is used as the dispersion medium for the arylsulfonamide alkali metal salt of general formula (2), the arylsulfonamide alkali metal salt (2) is not appreciably dissolved therein but a state of suspension can be successfully maintained throughout the reaction.

The method for addition of the aromatic isocyanate compound of general formula (3) to a suspension of the arylsulfonamide alkali metal salt of general formula (2) in said water-containing solvent typically comprises adding the compound (3) portionwise in powdery or liquid form or adding a solution of the compound (3) in a solvent.

In the latter case, the solution is preferably prepared by dissolving the aromatic isocyanate compound of general formula (3) in a solvent which is of the same kind as said water-containing solvent but is substantially free of water, particularly at least one solvent selected from the class consisting of acetonitrile, acetone, methyl ethyl ketone, diethyl ketone, methyl isobutyl ketone, tetrahydrofuran, ethyl acetate, and butyl acetate and substantially not containing water.

In the context of the present invention, the state of dispersion means a state of the reaction system in which the starting compounds and product compound are not completely dissolved in the solvent but form a heterogeneous system consistently from the beginning of reaction to completion of the reaction, preferably in a dispersed state. If a homogeneous solution is formed, the amount of byproducts tends to increase.

Since, in the present invention, the arylsulfonamide alkali metal salt of general formula (2) is not used in the form of an aqueous solution and the water content of said water-containing solvent is low, the starting compounds are not uniformly dissolved but remain suspended even in the early phase of the reaction.

The temperature of the reaction system at the time of addition of the aromatic isocyanate compound of general formula (3) to the suspension of the arylsulfonamide alkali metal salt of general formula (2) depends upon the reactivity of the specific aromatic isocyanate compound (3) but is preferably 0–70° C. and more preferably 10–50° C.

The duration of addition of the aromatic isocyanate compound of general formula (3) to the suspension of the arylsulfonamide alkali metal salt of general formula (2) is preferably 30 minutes–20 hours and more preferably 1–8 hours.

The reaction time following addition is preferably 30 minutes–2 hours and the reaction temperature is preferably equal to the temperature of the reaction mixture at the time of commencement of addition. The reaction goes to completion within 2 hours after addition but insofar as the temperature of the reaction mixture is maintained at 30° C. or below, stirring over hours exerts no particular adverse effect.

In the present invention, the water content of the water-containing solvent is 1–10 weight % and preferably 1–5 weight %. When the water content of this solvent is less than 1 weight %, the reaction between compounds (2) and (3) is retarded or does not proceed appreciably.

On the other hand, when the water content of said water-containing solvent exceeds 10 weight %, the aromatic isocyanate of general formula (3) tends to be hydrolyzed so that the formation of byproducts such as the compound formed as more than one molecules of the aromatic isocyanate form an urea bond will be increased to detract from the purity of the objective arylsulfonylureide compound.

When the aromatic isocyanate compound is added in the form of a solution in an organic solvent which is of the same kind as said water-containing solvent but substantially anhydrous to a suspension of the arylsulfonamide alkali metal salt of general formula (2) in said water-containing solvent, the water-content of the suspension decreases as the addition of said solution progresses but the water content of said suspension is preferably not more than 10% prior to said addition and not less than 1% after completion of the addition.

The arylsulfonamide alkali metal salt of general formula (2) can be obtained in the form of a suspension in toluene by dispersing the arylsulfonamide compound of general formula (2')

$$Ar^1\text{—}SO_2NH_2 \qquad (2')$$

wherein $Ar^1$ has the same meaning as $Ar^1$ in general formula (1) in toluene, adding an aqueous solution containing a stoichiometric amount of an alkali, and heating the suspension under azeotropic removal of water and toluene. Upon removal of toluene by filtration or distillation, the anhydrous arylsulfonamide alkali metal salt is then easily obtained.

The alkali metal that can be used includes lithium, sodium, potassium, etc., and whichever of an alkali metal hydride such as lithium hydride, sodium hydride, potassium hydride, etc., and an alkali metal hydroxide such as lithium hydroxide, sodium hydroxide, potassium hydroxide, etc., can be employed, although sodium hydroxide or potassium hydroxide is used with advantage.

Preferably an acid is permitted to act upon the arylsulfonylureide alkali metal salt of general formula (1') to liberate the alkali metal, whereupon the objective arylsulfonylureide compound is obtained.

The acid mentioned above is preferably a mineral acid such as hydrochloric acid, sulfuric acid, or nitric acid.

The acid to be added may be a diluted acid or a concentrated acid. This addition of an acid is preferably carried out until the pH falls within the range of 5–7, more preferably 6–7.

The solvent for use in this stage of removal of the alkali metal may be the very water-containing solvent mentioned hereinbefore but may be a suitable other solvent such as a solvent ether, e.g. diethyl ether or diisopropyl ether.

Optionally, the water-containing solvent or ether solvent mentioned above may be used in admixture with 1–5 parts by weight of water.

The arylsulfonylureide compound of general formula (1), which is available upon liberation of the alkali metal, can be recovered in high purity by rinsing off the concurrently formed inorganic salt with water and drying the product compound.

In the present invention, the step of reacting an arylsulfonamide alkali metal salt of general formula (2) with an aromatic isocyanate compound of general formula (3) and the step of removing the alkali metal from the resulting arylsulfonylureide alkali metal salt can be carried out using the same kind of solvent with high volume efficiency. Therefore, the technology is simple in procedure and advantageous in terms of production cost.

EXAMPLES

The following examples illustrate the present invention in further detail.

Example 1

In 61.4 g of acetonitrile with a water content of 4.7 weight % was dispersed 19.3 g of p-toluenesulfonamide sodium salt, and a solution of 12.5 g of diphenylmethane-4,4'-diisocyanate in 30 g of acetonitrile was added dropwise to the dispersion over 4 hours at 23–27° C. The water content of the reaction solvent at completion of dropwise addition was 3.17 weight %. After completion of dropwise addition, the reaction mixture was stirred at the same temperature for 1 hour. Then, after cooling to 15° C., 5.0 g of 98% sulfuric acid was added dropwise over 10 minutes at 15–20° C. The mixture was then stirred at that temperature for 2 hours, after which the precipitate was recovered by filtration, rinsed with 50 ml of water 4 times, and dried to provide 26.3 g (yield 90%) of white powders.

By NMR spectrometric analysis, elemental analysis, and infrared absorptiometric analysis, this compound was identified to be the objective 4,4'-bis[N'-(p-toluenesulfonyl)ureido]diphenylmethane. The purity of the compound as determined by high performance liquid chromatography was 98.1%.

Examples 2–6

Using the arylsulfonamide alkali metal salts mentioned in Table 1 in lieu of p-toluenesulfonamide sodium salt and the reaction solvents mentioned in Table 1 in lieu of said acetonitrile with a water content of 3.17 weight %, the procedure of Example 1 was otherwise repeated to provide the objective arylsulfonylureide compounds. Analyzed by the same methods as used in Example 1, the compounds were confirmed to be the objective compounds. The results are shown in Table 1.

Examples 7–9

Using tetrahydrofuran with a water content of 3.17 weight % (Example 7), ethyl acetate with a water content of 3.17 weight % (Example 8), and butyl acetate with a water content of 3.17 weight % (Example 9), respectively, in lieu of acetonitrile with a water content of 3.17 weight % as the reaction solvent, the procedure of Example 1 was otherwise repeated to provide the same objective compound.

Comparative Examples 1 and 2

Using the arylsulfonamide alkali metal salts mentioned in Table 1 in lieu of p-toluenesulfonamide sodium salt and the reaction solvents mentioned in Table 1 in lieu of acetonitrile with a water content of 3.17 weight %, the procedure of Example 1 was otherwise repeated to provide arylsulfonylureide compounds. Analyzed by the same methods as used in Example 1, those compounds were confirmed to be the objective compounds. The data are presented in Table 1.

Incidentally, in Comparative Example 1, the reaction substantially ceased to progress any further about 2 hours after commencement of dropwise addition of the acetonitrile solution of diphenylmethane-4,4'-diisocyanate and, therefore, the operation was discontinued.

Comparative Example 3

To 17.1 g of p-toluenesulfonamide were added 40 g of water and 4.8 g of sodium hydroxide, and the mixture was stirred to prepare a solution. This solution was diluted by adding 50 ml of acetone and a solution of 12.5 g of diphenylmethane-4,4'-diisocyanate in 150 ml of acetone was added dropwise over 1 hour. After completion of dropwise addition, the homogeneous starting material mixture was moderately refluxed for 2 hours. After the acetone was distilled off, 150 g of water was added to the residue and the insoluble matter was filtered off. The filtrate was adjusted to pH 2 with 5% hydrochloric acid. The precipitate which formed was recovered by filtration and dried to provide 14.0 g (yield 48%) of light-yellow powders.

The melting point of this compound was 120–130° C.

The purity of the compound as determined by high performance liquid chromatography was 70.6%.

TABLE 1

| Arylsulfonamide metal salt | Reaction solvent Water content of reaction solvent at completion of dropwise addition of the solvent | Yield (%) | Purity (%) |
|---|---|---|---|
| Ex. 1 | p-Toluenesulfonamide Na salt 19.3 g | Acetonitrile 3.17 wt. % | 90 | 98.1 |
| Ex. 2 | o-Toluenesulfonamide Na salt 19.3 g | Acetone 2.23 wt. % | 89 | 97.4 |
| Ex. 3 | 2-Naphthalenesulfonamide Na salt 22.9 g | Methyl ethyl ketone 2.50 wt. % | 91 | 97.3 |
| Ex. 4 | p-Chlorobenzenesulfonamide Na salt 21.4 g | Diethyl ketone 3.42 wt. % | 88 | 98.2 |
| Ex. 5 | Benzenesulfonamide Na salt 17.9 g | Methyl isobutyl ketone 3.73 wt. % | 87 | 97.6 |
| Ex. 6 | p-Toluenesulfonamide Na salt 19.3 g | Acetonitrile 6.8 wt. % | 83 | 96.7 |
| Comp. Ex. 1 | p-Toluenesulfonamide Na salt 19.3 g | Acetonitrile 0% | — | — |
| Comp. Ex. 2 | p-Toluenesulfonamide Na salt 19.3 g | Acetonitrile 12.0 wt. % | 76 | 90.0 |
| Comp. Ex. 3 | p-Toluenesulfonamide 17.1 g + NaOH 4.8 g | Acetone 20.2 wt. % | 48 | 70.6 |

By the process of the present invention, the objective arylsulfonylureide compound of high purity can be provided in good yield by a simple procedure.

What is claimed is:

1. A process for producing an arylsulfonylureide compound of general formula (1)

$$(Ar^1-SO_2NHCONH)_n-Ar^2 \qquad (1)$$

wherein $Ar^1$ represents an aromatic residue; $Ar^2$ represents a bivalent or trivalent aromatic residue; n represents an integer of 2 or 3; provided that when $Ar^2$ represents a bivalent residue, n is equal to 2 and that when $Ar^2$ is a trivalent residue, n is equal to 3 which comprises reacting an arylsulfonamide alkali metal salt of general formula (2)

$$Ar^1\text{—}SO_2NH.B \qquad (2)$$

wherein $Ar^1$ has the same meaning as $Ar^1$ in general formula (1); B represents an alkali metal with an aromatic isocyanate compound of general formula (3)

$$Ar^2\text{—}(NCO)_n \qquad (3)$$

wherein $Ar^2$ and n have the same meanings as $Ar^2$ and n, respectively, in general formula (1) in at least one solvent selected from the class consisting of acetonitrile, acetone, methyl ethyl ketone, diethyl ketone, methyl isobutyl ketone, tetrahydrofuran, ethyl acetate, and butyl acetate and containing 1 to 10 weight % of water in a state of suspension being maintained throughout the reaction and eliminating the alkali metal from the resulting arylsulfonylureide alkali metal salt in said solvent.

2. The process according to claim 1 wherein the reaction is carried out in at least one solvent containing 1–5 weight % of water.

3. The process according to claim 1 wherein $Ar^1$ in general formulas (1), (2) and (3) respectively represents phenyl or naphthyl, which phenyl and naphthyl may be substituted by $C_{1-6}$ alkyl, $C_{1-6}$ alkoxy, or halogen; $Ar^2$ represents 1,2-phenylene, 1,4-phenylene, 2,4-tolylene, 2,6-tolylene, 1,4-naphthylene, 1,5-naphthylene, 1,8-naphthylene, 2,6-naphthylene, methylenebis(1,4-phenylene), or 2,2-propylenebis(1,4-phenylene); B represents sodium or potassium; n is equal to 2.

4. The process according to claim 2 wherein $Ar^1$ in general formulas (1), (2) and (3) respectively represents phenyl or naphthyl, which phenyl and naphthyl may be substituted by $C_{1-6}$ alkyl, $C_{1-6}$ alkoxy, or halogen; $Ar^2$ represents 1,2-phenylene, 1,4-phenylene, 2,4-tolylene, 2,6-tolylene, 1,4-naphthylene, 1,5-naphthylene, 1,8-naphthylene, 2,6-naphthylene, methylenebis(1,4-phenylene), or 2,2-propylenebis(1,4-phenylene); B represents sodium or potassium; n is equal to 2.

* * * * *